United States Patent [19]

Manns et al.

[11] Patent Number: 5,319,436
[45] Date of Patent: Jun. 7, 1994

[54] MICROPLATE FARMING WELLS WITH TRANSPARENT BOTTOM WALLS FOR ASSAYS USING LIGHT MEASUREMENTS

[75] Inventors: Roy L. Manns, Marshfield Hills, Mass.; Alfred J. Kolb, Madison; Bernard S. Effertz, Meriden, both of Conn.

[73] Assignee: Packard Instrument Company, Inc., Downers Grove, Ill.

[21] Appl. No.: 890,030

[22] Filed: May 28, 1992

[51] Int. Cl.⁵ .............................................. G01N 21/03
[52] U.S. Cl. .................... 356/246; 356/440; 250/576
[58] Field of Search ............. 356/246, 244, 440, 317, 356/318; 250/576

[56] References Cited

U.S. PATENT DOCUMENTS

| | | | |
|---|---|---|---|
| 4,004,150 | 1/1977 | Natelson | 356/246 X |
| 4,154,795 | 5/1978 | Thorne | 422/99 |
| 4,251,159 | 2/1981 | White | 356/246 |
| 4,276,259 | 6/1981 | Eibl et al. | 422/71 |
| 4,431,307 | 2/1984 | Suovaniemi | 356/246 |
| 4,545,958 | 10/1985 | Dopatka | 422/102 |
| 4,652,553 | 3/1987 | Hagmann et al. | 514/26 |
| 4,735,778 | 4/1988 | Maruyama et al. | 422/102 |
| 4,741,619 | 5/1988 | Humphries et al. | 356/246 |
| 4,770,856 | 9/1988 | Uthemann et al. | 422/104 |
| 4,828,386 | 5/1989 | Matkovich et al. | 356/246 |
| 4,948,442 | 8/1990 | Manns et al. | 156/73.1 |
| 4,956,150 | 9/1990 | Henry | 356/246 X |
| 5,043,581 | 8/1991 | Joss | 250/328 |
| 5,047,215 | 9/1991 | Manns | 422/102 |
| 5,082,628 | 1/1992 | Andreotti et al. | 356/440 X |

FOREIGN PATENT DOCUMENTS

| | | |
|---|---|---|
| 446972 | 9/1991 | European Pat. Off. . |
| 449434 | 10/1991 | European Pat. Off. . |
| 2359422 | 2/1978 | France . |

*Primary Examiner*—Vincent P. McGraw
*Attorney, Agent, or Firm*—Arnold, White & Durkee

[57] ABSTRACT

A microplate forms a multiplicity of sample wells for holding samples to be assayed by light emissions or light transmission. The plate comprises an upper plate forming the side walls of the sample wells, the side walls being opaque so that light cannot be transmitted between adjacent wells through the side walls, and a lower plate forming the bottom walls of the sample wells, the bottom walls being transparent to allow the transmission of light therethrough. Bands of opaque material are provided within the lower plate and surrounding each well to block the transmission of light between adjacent wells through the lower plate.

18 Claims, 3 Drawing Sheets

MICROPLATE FARMING WELLS WITH TRANSPARENT BOTTOM WALLS FOR ASSAYS USING LIGHT MEASUREMENTS

Field of the Invention

The present invention relates generally to multi-well sample trays which are commonly referred to as microplates and which are used to hold a large number (e.g., 24, 48 or 96) of samples to be assayed by various techniques such as scintillation counting, luminometry, kinetics etc. This invention is particularly concerned with microplates for use in assaying techniques which require the emission of light from the sample, as occurs in scintillation counting, fluorimetry and luminometry, or the transmission of light through the sample.

BACKGROUND OF THE INVENTION

When microplates are used to hold samples to be assayed by techniques which are dependent on light emissions from the sample, it is important to avoid light transmission between adjacent samples, i.e., "crosstalk." Such crosstalk is extremely undesirable because it means that the photons detected in any particular sample well might not have originated from the particular sample in that well, and the purpose of the assaying technique is to obtain a unique measurement for each individual sample that is representative of only that sample.

In certain applications, it is desirable to have a transparent wall in the bottom of the sample well. For example, when coincidence measurement is used, it is desirable to have a first photodetector at the top of the well, which is normally open, and a second photodetector at the bottom of the well, which is normally closed. Of course, photons can be detected at the bottom of the well only if the wall of the well is transparent. Even when light measurements are not made at the bottom of the well, if is often desirable to have a transparent well wall to allow microscopic viewing of adherent cells within the well.

SUMMARY OF THE INVENTION

It is a primary object of the present invention to provide an improved microplate which includes a transparent wall which permits viewing of the sample and/or the measurement of light emissions from the sample, and yet avoids crosstalk between adjacent wells.

It is another important object of this invention to provide such an improved microplate which can be rapidly and efficiently manufactured.

Other objects and advantages of the invention will become apparent upon reading the following detailed description and upon reference to the accompanying drawings.

In accordance with the present invention, the foregoing objectives are realized by providing a microplate comprising an upper plate forming the side walls of the sample wells, the side walls being opaque so that light cannot be transmitted between adjacent wells through the side walls; a lower plate forming the bottom walls of the sample wells, the bottom walls being transparent to allow the transmission of light therethrough; and bands of opaque material within the lower plate and surrounding each well to block the transmission of light between adjacent wells through the lower plate. In a preferred embodiment, the bands of opaque material are formed by melting together the opaque material of the upper plate and the transparent material of the lower plate in preselected regions.

DESCRIPTION OF THE PREFERRED EMBODIMENTS

Figure 1:
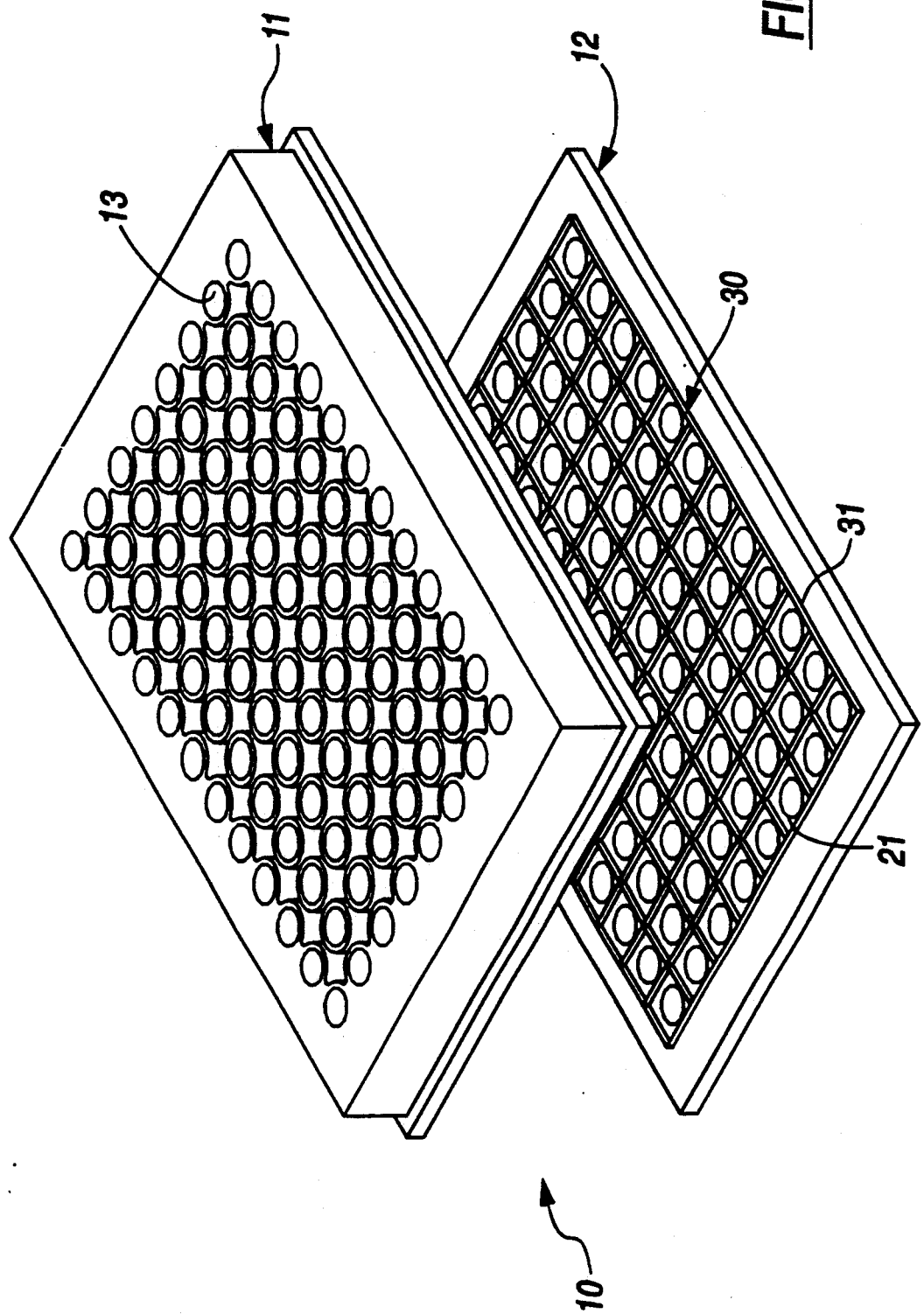
FIG. 1 is an exploded perspective view of a microplate embodying the present invention.
Figure 2:
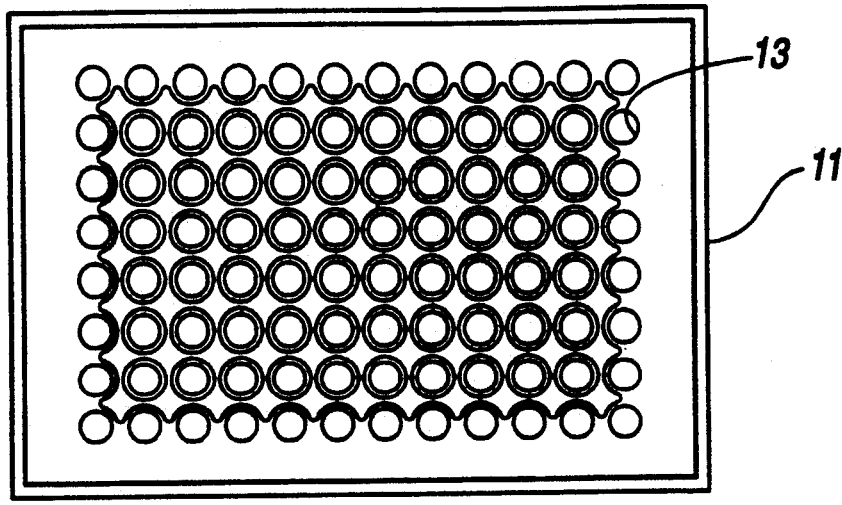
FIG. 2 is a top plan view of the upper portion of the microplate of FIG. 1.
Figure 3:
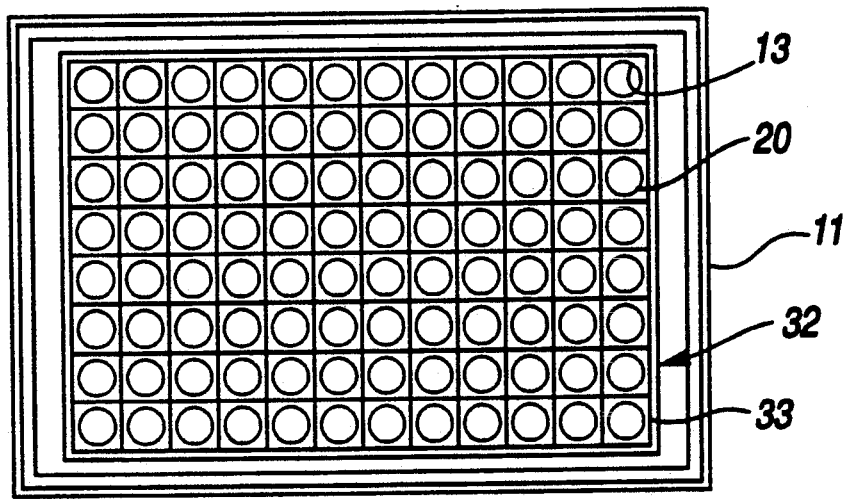
FIG. 3 is a bottom plan view of the upper portion of the microplate of FIG. 1.

While the invention is susceptible to various modifications and alternative forms, specific embodiments thereof have been shown by way of example in the drawings and will be described in detail. It should be understood, however, that it is not intended to limit the invention to the particular forms disclosed, but on the contrary, the intention is to cover all modifications, equivalents and alternatives falling within the spirit and scope of the invention as defined by the appended claims.

Turning now to the drawings and referring first to FIG. 1, there is shown a microplate 10 formed from two molded plastic plates 11 and 12. The upper plate 11 forms the side walls 13 of the multiple wells of the microplate, and in the illustrative example the wells are arranged in an 8×12 or 4×6 matrix. The bottom plate 12 forms the bottom walls 14 of the wells, and is attached to the lower surface of the upper plate 11 by fusing the two plates together. As will be described in more detail below, the fusion is preferably effected by ultrasonic bonding.

In order to confine light emissions to the well in which they originate, i.e., to prevent light transmission between adjacent wells, the upper plate 11 is formed from an opaque polymeric material so that light cannot be transmitted therethrough. For assaying techniques which require the detection of very small amounts of light, as in liquid scintillation counting, the pigmentation used to render the polymeric material opaque is preferably light in color so as to be highly reflective in order to ensure high counting efficiency with respect to the radioactive samples. To form an opaque light colored plate, a pigment having a high Albedo, preferably white, is added to the resin in an amount from about 2 to 20 weight percent. If a greater amount of pigment is added, the resin becomes too viscous for injection molding. The white pigment is selected from the group consisting of titanium dioxide, zinc oxide, zinc sulfide and thithopone. Titanium dioxide is generally more chemically resistant to scintillation cocktail solvents.

In certain types of luminescence and fluorescence assays it is preferred that the side walls 13 of the sample wells be non-reflective, in which case the upper plate 11 is preferably formed from a black or dark-colored polymer. The dark polymer may be formed by the addition of carbon black in amounts ranging from about 0.5 weight % to about 15 weight %.

In contrast to the upper plate 11, the lower plate 12 is formed of a transparent polymeric material so that it forms a transparent bottom wall 14 for each sample well. This permits viewing of sample material through the bottom wall 14, and also permits light emissions to be measured through the bottom wall. The transparent bottom walls 14 may also be used to expose the sample to light from an external excitation source, while leaving the tops of the wells unobstructed for maximum detection area. Examples of suitable transparent polymers are clear polystyrene, polyacrylonitrile, polycarbonate, polyester, polymethyl pentene and acrylic materials.

The transparent bottom walls of the wells are desirable in assaying techniques that measure light emitted from, or transmitted through, the sample in each individual well. Examples of such techniques are liquid scintillation counting, which counts light emissions produced by a radioactive sample in a liquid scintillator, and techniques which measure light emitted by luminescent labels, such as bioluminescent or chemiluminescent labels, fluorescent labels, or absorbance labels. These techniques use various types of light detectors, such as one or more photomultiplier tubes per well, solid state imaging devices with either lenses or fiber optic couplers, and fiber optic devices.

For any given assaying technique, the polymeric material chosen to form the plate must be nonreactive with, insoluble in, and impervious to the materials contained in the samples to be used in the assay. One particularly preferred resin is a copolymer containing at least 50 weight percent of an unsaturated nitrile monomer and a second monomer which is capable of being copolymerized with the unsaturated nitrile monomer. These high nitrile resins have excellent transparency, rigidity, processability and gas barrier resistance to oxygen, carbon dioxide and other gases. The resins are highly chemically resistant to solvents such as benzene, toluene, xylene, 1, 2, 4-trimethylbenzene (pseudocumene), alkobenzenes, diisopropyl napthalene, phenylxylylethane (PxE), heptane and ethyl acetate. One or more of the aforementioned solvents are usually present in liquid scintillation cocktails. Additionally, these resins form a microplate that does not deteriorate when exposed to ultraviolet light during storage.

Preferably, the unsaturated nitrile monomer of the above resins is selected from the group consisting of acrylonitrile and methacrylonitrile. The monomer capable of being copolymerized with the unsaturated nitrile is an ethylenically unsaturated copolymerizable monomer selected from the group consisting of alkyl acrylates, alkyl methacrylates, acrylic acid or methacrylic acid. According to one embodiment of the invention, the resin is a rubber modified acrylonitrile-methylacrylate copolymer containing about 75 weight percent acrylonitrile and about 25 weight percent methylacrylate. Such a rubber modified copolymer resin is commercially available under the trademark Barex 210-I ® resin manufactured by British Petroleum Chemicals Corporation.

For applications where the solvent resistance of the above-described copolymers is not required, polystyrene is a very cost-effective polymer that can be readily molded to form the plates 11 and 12.

Figure 4:
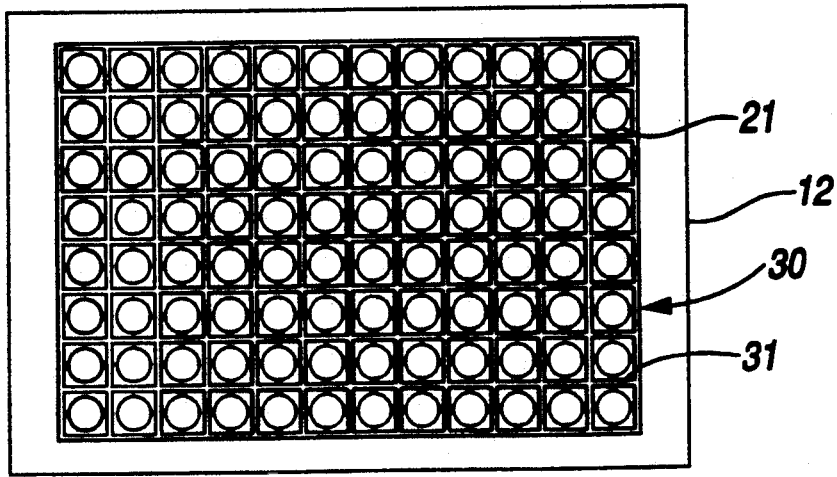
FIG. 4 is a top plan view of the lower portion of the microplate of FIG. 1.
Figure 5:
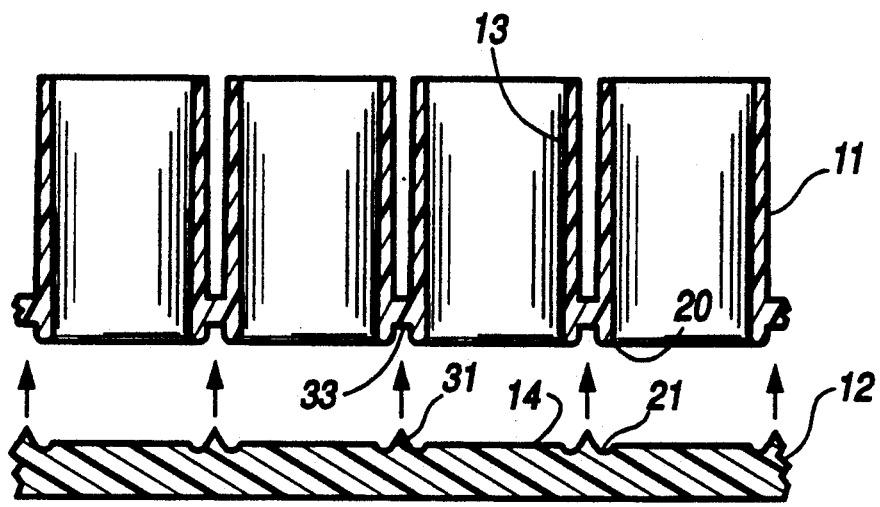
FIG. 5 is an enlarged section taken generally along line 5—5 in FIG. 1 and showing the two parts of the microplate before they have been joined to each other.
Figure 6:
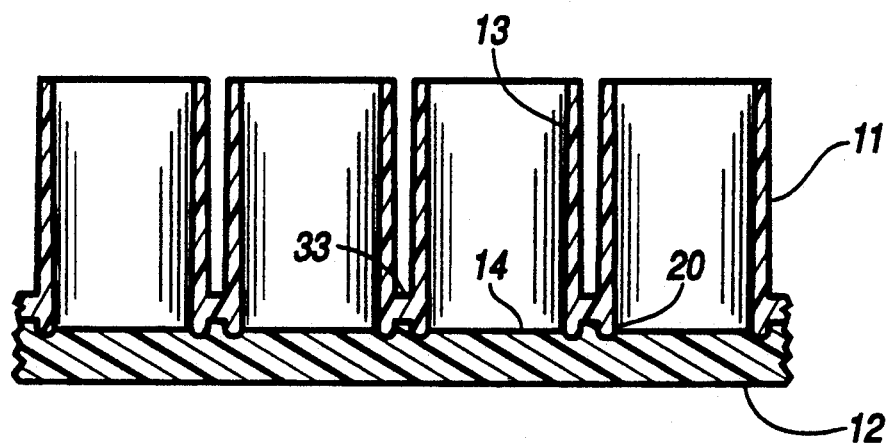
FIG. 6 is an enlarged section similar to FIG. 5 but showing the two parts of the microplate after they have been joined.
Figure 7:
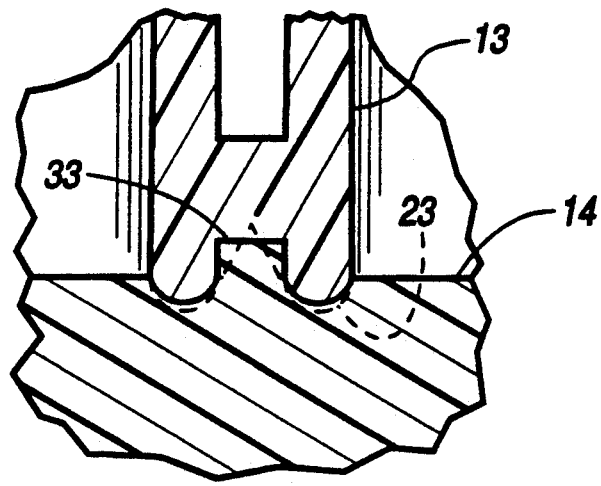
FIG. 7 is an enlargement of a portion of FIG. 6.

To form a barrier to the transmission of light between adjacent wells via the transparent bottom plate 12, a downwardly protruding bead 20 is formed around the entire circumference of each well opening on the bottom surface of the upper plate 11. As can be seen in FIG. 4, this bead 20 has a tapering cross-section, so that it is narrower at its bottom than at the top. When the two plates 11 and 12 are pressed together, each bead 20 fits into a circular groove 21 formed in the top surface of the lower plate 12. The vertical dimension of each bead 20 is at least as great as the depth of the groove 21, so that when the two plates are pressed together, the lowermost surfaces of the beads 20 are pressed into firm contact with the lower surfaces of the grooves 21.

The two plates 11 and 12 may be joined together by various processes, but the preferred process is ultrasonic bonding. In this process the two plates are held firmly pressed together while they are bonded by the application of ultrasonic energy which causes the contacting surfaces to fuse together. Because of the shape of the beads 20, they function as energy directors, causing the energy to be concentrated at the interface between the beads and the corresponding grooves and thereby ensuring that the beads 20 are melted within the grooves 21. This melting fusion causes the opaque polymer of the beads 21 to penetrate beneath the upper surface of the transparent lower plate 12. This forms a circular band 23 of opaque polymer around the transparent bottom wall of each well, thereby blocking the transmission of light between adjacent wells via the transparent bottom plate 12.

The beads 20 and grooves 21 should penetrate through 25% to 75% of the thickness of the transparent bottom plate 12 for effective reduction of optical cross talk. In a preferred embodiment, the bead and groove have a vertical dimension of 0.025 inch and the bottom plate 12 has a thickness of 0.060 inch. The inner edge of each groove is spaced 0.010 inch from the side wall of the corresponding wall.

Microplates formed in this manner have been found to significantly reduce optical and liquid crosstalk. For example, when used in liquid scintillation counting, liquid crosstalk is eliminiated and optical crosstalk is reduced from 2% or more to about 0.2% by the addition of the non-transmissive bands 23.

For the purpose of attaching the two plates 11 and 12 to each other, while at the same time forming an effective seal against liquid cross talk, a grid 30 of beads 31 is formed on the top surface of the lower plate 12. A similar grid 32 of grooves 33 is formed in the bottom surface of the upper plate 11 for receiving the bead grid 30. The height of the beads 31 is made substantially greater than the depth of the grooves 33 to ensure that the beads 31 are thoroughly melted to fill the grooves 33. For example, in a preferred embodiment the vertical dimensions of the beads 31 and the grooves 33 are 0.026 inch and 0.007 inch, respectively. With these dimensions, the application of ultrasonic energy thoroughly melts the beads 31.

The preferred ultrasonic bonding process may be effected by applying the energy to the lower plate 12 through a transducer or "horn" having a flat surface of about the same dimensions as the plate 12, with multiple recesses located in the same regions as the well holes in the upper plate 11. The recesses help to concentrate the ultrasonic energy in the regions between the wells.

An alternative to the ultrasonic bonding process described above is to mold the opaque upper plate 11 with the depending beads 20, and then mold the transparent lower plate 12 directly onto the bottom of the upper plate 11. The opaque beads 20 are thus embedded in the lower plate 12 to form the desired non-transmissive bands 23 between adjacent wells. It is also possible to use solvent or adhesives to fuse the two plates together.

While the invention has been described with particular reference to certain specific embodiments, it will be understood that various modifications may be made without departing from the spirit or scope of the invention. For example, the grooves in the top surface of the lower plate may be filled with opaque material from a source other than the beads on the lower surface of the upper plate. For example, the grooves could be filled with particulate or liquid opaque material. Also, in cases where a rigid bottom plate is not required, transparent bottom walls may be formed by applying a sheet of transparent film, such as polyester film, to the lower surface of the top plate 11 from which the beads 21 have been omitted. Such a film may be attached to the top plate 11 by means of adhesive, for example. Alternatively, the upper surface of the transparent film may be coated with another polymer such as polyethylene that will melt into the top plate.

We claim:

1. A microplate forming a multiplicity of sample wells for holding samples to be assayed by light emissions or light transmission, said plate comprising
    an upper plate forming the side walls of the sample wells, said side walls being opaque so that light cannot be transmitted between adjacent wells through said side walls, said upper plate being a single unitary molded plastic part,
    a lower plate forming the bottom walls of the sample wells, said bottom walls being transparent to allow the transmission of light therethrough, said lower plate being a single unitary molded plastic part, and
    bands of opaque material within said lower plate and surrounding the bottom wall of each well to block the transmission of light between adjacent wells through said lower plate.

2. The microplate of claim 1 wherein said upper plate is formed of a polymer which includes from about 2 to about 20 weight percent white pigment for opacity and reflectivity.

3. The microplate of claim 1 wherein said upper plate is formed of a polymer containing a pigment selected from the group consisting of titanium dioxide, zinc oxide, zinc sulfide, thithopane and black pigment containing 0.5% to 15% of carbon black.

4. The microplate of claim 1 wherein said upper plate is formed of a polymer which includes from about 0.5 to about 15 weight percent carbon black.

5. A microplate forming a multiplicity of sample wells for holding samples to be assayed by light emissions or light transmission, said plate comprising
    an upper plate forming the side walls of the sample wells, said side walls being opaque so that light cannot be transmitted between adjacent wells through said side walls,
    a lower plate forming the bottom walls of the sample wells, said bottom walls being transparent to allow the transmission of light therethrough, and
    bands of opaque material within said lower plate and surrounding each well to block the transmission of light between adjacent wells through said lower plate, said bands of opaque material being formed by melting together the opaque material of said upper plate and the transparent material of said lower plate in preselected regions.

6. A microplate forming a multiplicity of sample wells for holding samples to be assayed by light emissions or light transmission, said plate comprising
    an upper plate forming the side walls of the sample wells, said side walls being opaque so that light cannot be transmitted between adjacent wells through said side walls,
    a lower plate forming the bottom walls of the sample wells, said bottom walls being transparent to allow the transmission of light therethrough, and
    bands of opaque material within said lower plate and surrounding each well to block the transmission of light between adjacent wells through said lower plate, said bands of opaque material being formed from depending beads on the lower surface of said upper plate, each bead surrounding one of said wells, and said lower plate including grooves in the upper surface thereof for receiving said beads.

7. The microplate of claim 6 said beads on said upper plate are fused to said lower plate in said grooves.

8. The microplate of claim 7 wherein said beads are fused to said lower plate by ultrasonic bonding.

9. A method of assaying samples contained in a multi-well microplate by detecting light emitted from or transmitted through the sample in each well, said method comprising,
    placing the samples in a microplate comprising
        an upper plate forming the side walls of the sample wells, said side walls being opaque so that light cannot be transmitted between adjacent wells through said side walls, said upper plate being a single unitary molded plastic part,
        a lower plate forming the bottom walls of the sample wells, said bottom walls being transparent to allow the transmission of light therethrough, said lower plate being a single unitary molded plastic part, and
        bands of opaque material within said lower plate and surrounding each well to block the transmission of light between adjacent wells through said lower plate, and
    detecting light emitted from or transmitted through the sample in each separate well.

10. A microplate forming a multiplicity of sample wells for holding samples to be assayed by light emissions or light transmission, said microplate comprising a molded polymeric plate forming the side walls of the sample wells and made of an opaque material so that light cannot be transmitted between adjacent wells through said side walls, the bottom walls of the sample wells being formed by a sheet of transparent polymeric film attached to the lower surface of said plate to close the bottoms of the sample wells, and bands of opaque material within said film and surrounding each well to block the transmission of light between adjacent wells through said film.

11. The microplate of claim 10 wherein said polymeric film is polyester film.

12. The microplate of claim 10 wherein said polymeric film is bonded to the lower surface of said plate.

13. The microplate of claim 10 wherein said side walls of the sample wells are reflective.

14. A method of assaying samples contained in a multi-well microplate by detecting light emitted from the sample in each well, said method comprising,
    placing the samples in a microplate comprising
        a plate forming the side walls of the sample wells, said side walls being opaque so that light cannot be transmitted between adjacent wells through said side walls, and a sheet of transparent polymeric film attached to the lower surface of said plate to close the bottoms of the sample wells, bands of opaque material within said film surrounding each well to block the transmission of light between adjacent wells through said film, and detecting light emitted from the sample in each separate well.

15. The method of claim 14 wherein said polymeric film is polyester film.

16. The method of claim 14 wherein said polymeric film is bonded to the lower surface of said plate.

17. The method of claim 14 wherein said side walls of the sample wells are reflective.

18. The method of claim 14 wherein the light emitted from said samples is detected by scintillation counting.

* * * * *